(12) United States Patent
Ducheyne et al.

(10) Patent No.: US 6,328,990 B1
(45) Date of Patent: Dec. 11, 2001

(54) BIOACTIVE, DEGRADABLE COMPOSITE FOR TISSUE ENGINEERING

(75) Inventors: Paul Ducheyne, Rosemont; Portonovo S. Ayyaswamy, Broomall, both of PA (US); Qing-Qing Qiu, Kingston (CA)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/439,183

(22) Filed: Nov. 12, 1999

(51) Int. Cl.⁷ ..................................................... A61F 2/00
(52) U.S. Cl. .................. 424/426; 424/423; 424/422; 424/428; 424/484; 424/486; 424/489; 623/11
(58) Field of Search ..................................... 424/426, 423, 424/422, 428, 484, 486, 489; 623/11

(56) References Cited

U.S. PATENT DOCUMENTS

| | | | |
|---|---|---|---|
| 5,556,642 | * | 9/1996 | Kobayashi et al. ................. 424/502 |
| 5,626,861 | * | 5/1997 | Laurencin et al. ................... 424/426 |
| 5,964,807 | * | 10/1999 | Gan et al. ............................. 623/17 |
| 6,197,342 | * | 3/2001 | Thut te al. ........................... 424/484 |

OTHER PUBLICATIONS

Zhang R. and Ma, P.X. Porous poly (l–lactic acid)/apatite composites created by biomimetic process. 1998. Dept. of Biologic and Biomedical Engineering, 285–293.*

Alberton et al., "Preparation and Characterisation of Poly(a-dipic anhydride) Microspheres for Ocular Drug Delivery", *Jour. of Applied Polymer Science* 1996 62:695–705.

Baker et al., "The bone–bonding polymer Polyactive 80/20 induces hydroxycarbonate apatite formation in vitro", *Jour Biomedical Materaial Research* 1997 34:79–86.

Hench L., "Bioactive Ceramics", *Bioactive Ceramics*, Part II, 54–71.

Kokubo et al., "Solutions able to reproduce in vivo surface–structure changes in bioactive glass–ceramic A–W³", 1990 *Journ Biomedical Materials Research*, 24:721–734.

Mathiowitz et al., "Polyanhydride Microspheres as Drug Carriers. II. Microencapsulation by Solvent Removal", *Journal of App Polymer Science* 1988, 35: 755–774.

Mathiowitz et al., "Polyanhydride microspheres: 3. Morphology and characterization of systems made by solvent removal", *Polymer* 1990 31:547–554.

Qiu et al., "Formation and Differentiation of Three–Dimensional Rat Marrow Stromal Cell Culture on Microcarriers in a Rotating–Wall Vessel", *Tissue Engineering* 1998 4:19–26.

Qui et al., "Fabrication, characterization and evaluation of bioceramic hollow microspheres used as microcarriers for 3–D bone tissue formation in rotating bioreactors", *Biomaterials* 20, 1999 989–1001.

Radin et al., "The effect of calcium phosphate ceramic compositon and structure on in vitro behavior. II Precipitation", *Jour Biomedical Materials Research* 1993 27:35–45.

Uchida, et al., "Preparation and Characterization of Polylactic Acid Microspheres Containing Bovine insulin by a w/o/w Emulsion Solvent Evaporation Method", *Chem. Pharm. Bull.* 1997 45(9): 1539–1543.

Vert et al., "Bioresorable Plastic Materials for Bone Surgery", *Macromolecular Biomaterials*, Chapter 6: 119–142.

Wakiyama et al., "Preparation and Evaluation in Vitro and in Vivo Polylactic Acid Microspheres containing Dibucaine", *Chem. Pharm Bull* 1982 3719–3727.

Zhang et al., "Porous poly ($_L$ –lactic acid)/apatite composites created biomimetic process", *Dept of Biologic and Materials Sciences and Biomedical Engineering*, 1998 285–293.

* cited by examiner

*Primary Examiner*—Thurman K. Page
*Assistant Examiner*—Liliana Di Nola-Baron
(74) *Attorney, Agent, or Firm*—Licata & Tyrrell P.C.

(57) ABSTRACT

Bioactive, degradable composite material and composite material microspheres were produced using a new solid-in-oil-in-water method. Compositions and methods for tissue engineering and drug delivery are provided.

18 Claims, No Drawings

BIOACTIVE, DEGRADABLE COMPOSITE FOR TISSUE ENGINEERING

This invention was made in the course of research sponsored by National Aeronautics and Space Administration. The U.S. Government may have certain rights in this invention.

BACKGROUND OF THE INVENTION

Since 1967 when van Wezel introduced and demonstrated the use of small globular particles as support for growth of anchorage-dependent cells in suspended cultures, a variety of composite materials and microspheres have been used in 3-dimensional (3D) cell cultures. They include dextran microspheres, polystyrene microspheres, polyacrylamide microspheres, and silica glass beads to name a few. Microcarriers made from degradable polymers have found applications in sustained delivery of drugs or other biologically active compounds (Uchida et al. 1997. *Chem. Pharm. Bull.* 45:1539–1543; Wakiyama et al. 1982. *Chem. Pharm. Bull.* 30:3719–3727; Mathiowitz et al. 1988. *J. Appl. Polym. Sci.* 35:755–774; Mathiowitz et al. 1990. *Polymer* 31:547–555; Albertson et al. 1996. *J. Appl. Polym. Sci.* 62:695–705).

Calcium phosphate-based ceramics and glasses have the ability to bond with bone tissues and have been widely used in bone repair (Ducheyne, P. and J. Lemons. 1988. *Ann. NY Acad. Sci.* 523). Based on a comparison of literature data it was suggested that 45S5 "bioactive" glass (45% $SiO_2$, 24.5% $Na_2O$, 24.5% CaO, and 6% $P_2O_5$) had the highest rate of bonding to bone (Hench, L.L. 1988. *Ann. NY Acad. Sci.* 523:54–71), where "bioactive" means the material has the ability to interact or bind to living tissue. Recently, 45S5 bioactive glass has been considered for use as bioactive ceramic microspheres in 3D bone cell cultures in rotating bioreactors (Qiu et al. 1998. *Tissue Engineer.* 4:19–34). The use of bone bioactive materials is of great interest in bone synthesis in vitro because of their ability to promote cell-material bonding and the potential to enhance bone formation.

It is believed that the presence and formation of calcium hydroxyapatite at the implant-bone interface is critical for bone bonding and is one of the key features necessary for successful bioactive bone implants. Calcium hydroxyapatite coatings on implants or calcium hydroxyapatite blocks have been used to produce implants with bone-binding abilities. Through use of an in vitro immersion method using a simulated physiological solution, a solution that mimics the ion concentration in body fluids, the formation of the calcium hydroxyapatite layers on bioactive glasses, bioactive glass-ceramics and polymers have been produced and this method of "in vitro immersion" used to predict bone-bonding potential of bone implant materials (Kokubo et al. 1990. *J. Biomed. Mater. Res.* 24:721–734; Li et al. 1997. *J. Biomed. Mater. Res.* 34:79–86).

Solid bioceramic microspheres typically have a density higher than 2 $g/cm^3$. When they are used in bioreactors, the solid ceramic microspheres experience a high shear stress which causes cell detachment and damage (Qiu et al. 1998. *Tissue Engineer.* 4:19–34). This problem has been solved by reducing the apparent density of the microspheres through a hollow structure approach (Qiu et al. 1999. *Biomaterials* 20:989–1001). Cell culture studies have confirmed that the hollow bioceramic microspheres ($SiO_2/Al_2O_3$/CaP) experience a low shear stress and can support 3D bone cell cultures in rotating bioreactors. However, because of their non-degradable component, $Al_2O_3$, hollow bioceramic microspheres cannot be completely replaced by bone tissues. New microcarriers that are bioactive, degradable and with a density low enough to produce a low shear stress, are desired.

A new bioactive and degradable composite material has been developed for use in 3-dimensional bone tissue engineering and bone implant materials.

SUMMARY OF THE INVENTION

An object of the present invention is a bioactive, degradable composite material where the composite is made from mixing a modified bioactive glass powder with a poly(lactic co-glycolic acid) polymer matrix. The composite may be used in tissue engineering for implantation or as a microcarrier for delivery of drugs.

Another object of the present invention is a solid-in-oil-in-water solvent removal method for production of bioactive, degradable composite materials, including microspheres.

Yet another object of the present invention is a method for inducing bone regeneration in an animal and a method for drug delivery in an animal.

Yet another object of the present invention is a method for producing bioactive and degradable scaffolds for 3-dimensional bone tissue engineering.

DETAILED DESCRIPTION OF THE INVENTION

There is a need for composite materials, including microspheres, for tissue engineering, such as bone implants, that are bioactive (i.e., can bond to living tissue such as bone) and resorbable or degradable (i.e., can be replaced by tissue after a period of implantation). In addition to acting as an implant material, such composites could be used as drug delivery devices for tissue regeneration.

A solid-in-oil-in-water (s/o/w) solvent removal process was developed for the fabrication of a bioactive and degradable composite material. This method differs from previous methods (Uchida et al. 1997. *Chem. Pharm. Bull.* 45:1539–1543) where a water-in-oil-in-water (w/o/w) solvent removal method was used. Modified 45S5 bioactive glass powders are used in this new method as the solid filler phase. Among the degradable polymers available, poly (lactic co-glycolic acid) polymers (PLGA) are known to have a wide range of physical, thermal, mechanical and biological properties and have been used successfully in implants and drug delivery systems for bone regeneration (Vert et al. 1984. In: *Macromolecular Biomaterials*, Hastings, G.W. and P. Ducheyne (eds.), CRC Press: Boca Raton, pp. 120–142). Each of the constituent monomers can be present in concentrations ranging from 0 to 100%. Therefore, PLGA was chosen as the polymer matrix of the composite material of the present invention.

Glass powders with a size <20 µm and a composition of 45% $SiO_2$, 24.5% CaO, 24.5% $Na_2O$, and 6% $P_2O_5$ (in % by weight) were used. The glass powders were modified by immersion in a 0.05 M Tris buffer (pH 7.3) supplemented with plasma electrolyte (a simulated physiological solution; ion concentrations as in Radin, S.R. and P. Ducheyne 1993. *J. Biomed. Mater. Res.* 27:35–45) at 37° C. The immersed particles were shaken and incubated from 1 hour to 3 days. The simulated physiological solution was changed every 2 hours for the first 6 hours and then changed at 24, 48 and 72 hours. Fourier transform infrared spectroscopy (FTIR) was used to examine the FTIR spectra of the glass powders after immersion for 1 hour, 6 hours, 1 day and 3 days.

After immersion in simulated physiological solution for 6 hours, amorphous calcium phosphate was formed as indicated by the presence of a bending vibration mode of the $PO_4$ groups (P—O bend). After immersion for 1 day, the P—O bend peak divided, indicating the presence of crystalline calcium phosphate ceramic phase. The appearance of bands located at 870 $cm^{-1}$ (C—O bonds) and 960 $cm^{-1}$ (P—O symmetric stretch, characteristic of hydroxyapatite) indicated that the crystalline phase could be identified as carbonated calcium hydroxyapatite. Monitoring of the pH changes over time demonstrated that when bioactive glass powders were immersed in simulated physiological solution, pH increased with time. After 3 days of immersion, there was little pH change. When bioactive glass particles were used without modification in the preparation of the composites, the composite material surface was severely cracked. It was found unexpectedly that this problem could be avoided by pre-immersing the glass powders. For instance, bioactive glass particles immersed for 3 days were used in preparation of microspheres of the composite material of the present invention.

Polylactic acid (PLA) microspheres (100% lactic acid, no glycolic acid used in the polymer) were prepared from PLA concentrations of 0.2, 0.4, 0.6 and 0.8 g in 5 ml methylene chloride. The quantitative analysis of particle size distribution revealed that the distribution of microsphere size was affected by the concentration of the PLA in methylene chloride. An increase in PLA concentration in methylene chloride resulted in an increase in the mean particle size of microspheres. Since microcarriers with a size range of 100-200 $\mu$m was desired for cell culture studies, PLA concentrations of 0.6 g in 5 ml methylene chloride were chosen for the preparation of PLA-bioactive glass microspheres.

A s/o/w emulsion solvent evaporation method was developed. To begin, 600 mg of PLA (Alkermes, OH) was dissolved in 5 ml methylene chloride. Then, 600 mg of modified bioactive glass powder was mixed with the PLA solution and sonicated for 15 minutes. The mixture was then added drop by drop into 200 ml 0.5% (w/v) polyvinyl alcohol water solution. This mixture was stirred for 4 hours at room temperature and then the microspheres collected by centrifugation. The microspheres were filtered, washed with water and then dried at room temperature in a desiccator.

Incorporation of modified bioactive glass powders into the microspheres was demonstrated by light microscopy and scanning electron microscopy analyses. Scanning electron microscopy (SEM) revealed that the microspheres were mostly covered by PLA and that there were micron-size pores in the microsphere surface. Cross-sectional analysis showed that the glass powders were distributed in the outer polymeric shell of the microsphere. The microsphere had a hollow structure inside and the modified glass particles were embedded in the porous polymer matrix. The microspheres were closed and energy dispersive x-ray (EDX) analysis of the microsphere cross-section further confirmed the presence of silicon, calcium and phosphorus. After 2 weeks of immersion in simulated physiological solution, microspheres were fully covered by a calcified layer that consisted of 2 to 3 $\mu$m globules. Calcium and phosphate were detected in the calcified surface of the composite microspheres by SEM combined with energy dispersive x-ray analysis (EDX). FTIR analysis on the microspheres after 3 weeks of immersion demonstrated the presence of carbonated crystalline calcium hydroxyapatite as indicated by the presence of orthophosphate bands (P—O at 560, 606, 950 and 1044 $cm^{-1}$) and C—O bands (C—O at 1410 and 874 $cm^{-1}$).

These results demonstrated the successful production of bioactive and biodegradable composite material and microspheres of the composite material for use in tissue engineering and regeneration. The composite material has an advantage over prior art composites in terms of the bioactivity conferred by the use of modified bioactive glass and the biodegradability conferred by use of both the polyester polymer and the glass. Hydroxyapatite and other calcium phosphates which had been used before were not able to be resorbed. Size of composite microspheres was controlled with this method, another advantage over previous methods. Because the degradation product of PLA can be metabolized by the body, PLA makes an excellent implant material and an excellent carrier for controlled drug delivery of a wide range of bioactive agents in animals, including humans. The use of bioactive glass with PLA creates an alkaline environment that when in contact with body fluid may neutralize the lactic acid produced with biodegradation and limit potential local inflammatory responses often seen with implanted PLA.

The use of simulated physiological fluid as a way to predict bone-bonding ability of implanted materials demonstrated that the composite material and the microspheres of the present invention have the potential to bond with tissue and that bone bonding would be expected in vivo. The acquisition of calcium hydroxyapatite over the complete surface of the composite material microspheres provides a support for new bone formation and links the bone or tissue with the implant.

The reactivity of the composite material microspheres was explored in more detail by examining the formation of the mineral layer on the surface of the microspheres with the in vitro immersion method (in simulated physiological solution). Changes in concentrations of calcium (Ca), phosphate ($PO_4$) and silicon (Si) in the immersion solutions as a function of incubation time were also analyzed using standard wet chemical methods.

Composite microspheres prepared by the methods described here were immersed in simulated physiological fluid at a particle-to-solution ratio equal to 5 mg per 10 ml at 37° C. for 1 hour to 3 weeks. Microspheres and solution samples were collected at different time points during the immersion period. Solution chemical analysis revealed that Ca and $PO_4$ concentration changes decreased with incubation time in the solutions containing the composite microspheres whereas there was no detectable change throughout the 3 week period in solution where non-composite PLA microspheres (control microspheres) were incubated. The rate of Ca and $PO_4$ uptake decreased after 2 days of immersion of the composite microspheres and after 2 weeks the ratio of Ca and $PO_4$ uptakes was about 1.3. Release of Si from composite microspheres was continuous over time, with the rate of release decreasing after 2 days of immersion. This decrease in Si release rate coincided with the decreased uptake of Ca and $PO_4$. These data indicated that the silicate ions leached from the bioactive glass attached on the polymeric surface and served as nucleation sites. Because the bioactive glass powders were encapsulated inside the microspheres, Si leaching was a time-dependent and dynamic process, keeping the surface of the microsphere reactive during the immersion period.

For the SEM and EDX analysis, PLA microspheres again served as controls. After 1 week of immersion, no mineral deposition was evident on the surface of PLA microspheres and after 3 weeks, cracks appeared on their surface indicating a degradation of PLA polymer. In contrast, composite microspheres formed a large number of microparticles on their surface after 1 week of immersion. Most of the microparticles appeared to be growing out of pores and along cracks in the polymeric surface. After 2 weeks of immersion, the surfaces of the composite microspheres were mostly covered by microparticles with a diameter up to 3 μm. The granules were assembled into small flake-like pieces. The surfaces of the composite microspheres were fully covered by a layer of mineral after 3 weeks of incubation. Cracks were observed in the mineral layer.

EDX analysis revealed that only carbon and oxygen peaks were detected on the surfaces of PLA microspheres after a 3 week immersion. In contrast, Si, Ca and phosphorus (P) were detected on the surfaces of composite microspheres after 4, 7 and 21 days of immersion. The calcium to phosphate ratios of the surface layers varied from 1.1 to 1.4 on the composite microspheres immersed in simulated physiological fluid from 4 days to 3 weeks. Traces of chloride, sodium and magnesium were also detected in the calcium-phosphate-rich layers after 1 and 3 weeks of immersion.

FTIR spectra of the composite microspheres immersed for 2 and 3 weeks showed $(PO_4)^{3-}$ bands at 1098, 1046, 60 and 561 $cm^{-1}$. These bands represented crystalline calcium hydroxyapatite. The intensity of the phosphate bands increased with immersion time. In the spectra of the composite microspheres immersed for 3 weeks, carbonate bands at 1410 and 874 $cm^{-1}$ were evident, indicating the formation of carbonated calcium hydroxyapatite.

These results demonstrated that the PLA/bioactive glass microspheres synthesized using the s/o/w process induced formation of carbonated calcium hydroxyapatite and transformed the polymeric surface fully into carbonated calcium hydroxyapatite after immersion in simulated physiological fluid for 3 weeks. Formation of a layer of a biologically active apatite, such as carbonated calcium hydroxyapatite, at the implant-bone surface during implantation is essential for implant bonding to living bone tissue. Therefore, the composite microspheres of the present invention are shown to be capable of interacting with living tissue to form a bond.

The composite material microspheres of the present invention were almost fully covered by a calcium-phosphate-rich layer after only 2 weeks of immersion; in contrast no mineral deposition was seen on the surfaces of PLA microspheres. Previous research has shown that poly (L-lactic acid) scaffolds, take much longer to induce formation of a surface layer (which was hydroxyapatite)even with a solution greatly over saturated in Ca and P (Zhang, R. and P.X. Ma. 1999. *J. Biomed. Mater. Res.* 45:285–293). Furthermore, it has been shown that bioactive glass surface reaction layers have a much greater effect on bone cell function than regular hydroxyapatite (Garcia, A. et al. 1998. *J. Biomed. Mater. Res.* 40:48–56;).

The formation of the calcium-phosphate layer on the composite microspheres clearly suppressed degradation as PLA microsphere degradation was evident in the current studies after 3 weeks. It appears that the modified bioactive glass powder of the composite microsphere neutralizes the accumulated acid and slows degradation. The surface reaction layer that forms also protects the polymer from degradation. The slowed degradation of the composite microspheres would allow additional time for bone healing across an implant surface before degradation of the composite microspheres was completed.

Using a new method for composite material preparation, bioactive and degradable material and microspheres made of the same composite material have been produced. The composite material is composed of a modified bioactive glass powder incorporated into a poly alpha hydroxy acid substance that would include but not be limited to polylactic acid, polyglycolic acid, and their copolymers. The ability of the composite material to induce formation of carbonated calcium hydroxyapatite on its surface, the major inorganic component of bone, demonstrates the bone-bonding ability of this composite material and microspheres of this composite material in vivo. In addition, because of the microsphere's spherical shape and a density that is close to that of culture medium, these microspheres can act as microcarriers for 3-dimensional tissue engineering in bioreactors or other tissue culture devices. Moreover, because of their biodegradability, these composite microspheres could be used as drug delivery devices. The composite material and the composite material microspheres of the present invention would be used as both implant material in 3-dimensional tissue engineering and microcarriers depending on the condition to be treated in an animal, including humans.

What is claimed is:

1. A bioactive, degradable composite material comprising a modified, bioactive glass powder incorporated into a poly(lactic co-glycolic acid) polymer matrix.

2. The bioactive, degradable composite material of claim 1 wherein said composite material is coated with a silicon-containing calcium phosphate film.

3. The bioactive, degradable composite material of claim 1 wherein said composite material is in the form of a microsphere.

4. The bioactive, degradable composite material of claim 2 wherein said composite material is in the form of a microsphere.

5. The bioactive, degradable composite material of claim 1 wherein said composite material is in the form of a hollow microsphere.

6. The bioactive, degradable composite material of claim 2 wherein said composite material is in the form of a hollow microsphere.

7. The bioactive, degradable composite material of claim 3 further comprising a drug.

8. The bioactive, degradable composite material of claim 4 further comprising a drug.

9. The bioactive, degradable composite material of claim 5 further comprising a drug.

10. The bioactive, degradable composite material of claim 6 further comprising a drug.

11. A solid-in-oil-in-water solvent removal method for production of a bioactive, degradable composite material for tissue engineering comprising:

a) dissolving a poly(lactic co-glycolic acid) polymer in methylene chloride to produce a poly(lactic co-glycolic acid) polymer solution;

b) mixing a modified bioactive glass powder with the poly(lactic co-glycolic acid) polymer solution to produce a poly(lactic co-glycolic acid) polymer-bioactive glass powder solution; and c) adding the poly(lactic co-glycolic acid) polymer-bioactive glass powder solution drop by drop into a polyvinyl alcohol solution to produce a composite material for tissue engineering.

12. A method for inducing bone regeneration in an animal comprising implanting the bioactive, degradable composite material of claim 1.

13. A method for drug delivery in an animal comprising administering bioactive, degradable composite material of claim 7.

14. A method for drug delivery in an animal comprising administering bioactive, degradable composite material of claim 8.

15. A method for drug delivery in an animal comprising administering bioactive, degradable composite material of claim 9.

16. A method for drug delivery in an animal comprising administering bioactive, degradable composite material of claim 10.

17. A method for 3-dimensional bone tissue engineering in bioreactors and other tissue culture devices comprising seeding the bioactive, degradable composite material of claim 3.

18. A method for 3-dimensional bone tissue engineering in bioreactors and other tissue culture devices comprising seeding the bioactive, degradable composite material of claim 4.

* * * * *